(12) United States Patent
Pernodet et al.

(10) Patent No.: US 10,149,811 B2
(45) Date of Patent: Dec. 11, 2018

(54) METHODS AND COMPOSITIONS FOR STIMULATING COLLAGEN SYNTHESIS IN SKIN CELLS

(71) Applicant: ELC Management LLC, Melville, NY (US)

(72) Inventors: Nadine Pernodet, Huntington Station, NY (US); Krystle Corallo, Huntington, NY (US)

(73) Assignee: ELC Management LLC, Melville, NY (US)

(*) Notice: Subject to any disclaimer, the term of this patent is extended or adjusted under 35 U.S.C. 154(b) by 196 days.

(21) Appl. No.: 15/041,602

(22) Filed: Feb. 11, 2016

(65) Prior Publication Data

US 2017/0231890 A1    Aug. 17, 2017

(51) Int. Cl.
| | | |
|---|---|---|
| *A61K 8/64* | (2006.01) | |
| *A61Q 19/08* | (2006.01) | |
| *C07K 5/083* | (2006.01) | |
| *C07K 7/06* | (2006.01) | |
| *A61K 8/97* | (2017.01) | |
| *A61K 8/98* | (2006.01) | |

(52) U.S. Cl.
CPC ............... *A61K 8/64* (2013.01); *A61K 8/975* (2013.01); *A61K 8/986* (2013.01); *A61Q 19/08* (2013.01); *C07K 5/081* (2013.01); *C07K 7/06* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 5,980,916 A * | 11/1999 | Yvin ................ | A61K 8/73 424/401 |
| 8,193,155 B2 | 6/2012 | Maes et al. | |
| 8,703,161 B2 | 4/2014 | Maes et al. | |
| 8,962,571 B2 | 2/2015 | Maes et al. | |
| 9,115,212 B2 | 8/2015 | Hornebeck et al. | |
| 9,687,439 B1 * | 6/2017 | Pernodet ................ | A61K 36/03 |
| 2007/0110731 A1 | 5/2007 | Riley | |
| 2009/0220481 A1 * | 9/2009 | Maes ..................... | A61K 8/645 424/94.61 |
| 2010/0129305 A1 | 5/2010 | Lee et al. | |
| 2011/0269694 A1 * | 11/2011 | Dal Farra ................ | A61K 8/64 514/18.8 |
| 2014/0301958 A1 | 10/2014 | Bojanowski et al. | |
| 2015/0098963 A1 | 4/2015 | Pernodet et al. | |

FOREIGN PATENT DOCUMENTS

| | | |
|---|---|---|
| CN | 105025874 | 11/2015 |
| EP | 1129699 | 9/2001 |
| FR | 2989276 | 10/2013 |
| KR | 20150120426 | 10/2015 |
| WO | WO-2008/136676 | 11/2008 |
| WO | WO-2016/133775 | 8/2016 |

OTHER PUBLICATIONS

Christina Burnett. Safety Assessment of Soy Peptides as Used in Cosmetics. Cosmetic Ingredient Review. May 22, 2015. (Year: 2015).*

PCT International Search Report; International Application No. PCT/US2017/015007; Completion Date: Apr. 27, 2017; dated Apr. 27, 2017.

PCT Written Opinion of the International Searching Authority; International Application No. PCT/US2017/015007; Completion Date: Apr. 27, 2017; dated Apr. 27, 2017.

* cited by examiner

*Primary Examiner* — Marcela M Cordero Garcia
*Assistant Examiner* — Jia-Hai Lee
(74) *Attorney, Agent, or Firm* — Julie M. Blackburn

(57) ABSTRACT

A composition comprising a first peptide selected from tripeptide, tetrapeptide and mixtures thereof; a second peptide selected from pentapeptide, hexapeptide, and mixtures thereof; an extract from the *Laminaria* genus, and whey protein, and a method for stimulating collagen synthesis in skin cells.

23 Claims, No Drawings

Specification includes a Sequence Listing.

METHODS AND COMPOSITIONS FOR STIMULATING COLLAGEN SYNTHESIS IN SKIN CELLS

TECHNICAL FIELD

The invention is in the field of compositions for treating aging skin, and with particular efficacy in stimulating synthesis of collagen in skin cells.

BACKGROUND OF THE INVENTION

Collagen is one of the main structural proteins in skin. It can be found in the fibrillar or non-fibrillar form. The fibrillar form is most common and includes collagen subtypes I, II, III, V, and XI. Types I, IV, and V are most often associated with skin and dermal tissue. Collagen found in the skin typically diminishes with age and causes laxity, lines, and wrinkles on skin. Any active ingredient that induces skin cells to increase collagen synthesis is desirable because it ameliorates the adverse effects of collagen deficiency in skin cells which causes lines, wrinkles, and skin laxity.

It has been discovered that certain tripeptides or tetrapeptides have a synergistic effect in stimulating collagen synthesis in skin cells when combined with a combination of at least one pentapeptide or hexapeptide, at least one extract from *Laminaria* genus, and whey protein.

SUMMARY OF THE INVENTION

The invention is directed to a topical composition comprising a first peptide selected from a tripeptide, tetrapeptide or mixtures thereof; a second peptide selected from the group consisting of a pentapeptide, hexapeptide, or mixtures thereof, at least one extract from the *Laminaria* genus, and whey protein.

The invention is also directed to a method for stimulating collagen synthesis in skin cells by topically applying a composition comprising at least one first peptide selected from a tripeptide, tetrapeptide, or mixtures thereof; at least one second peptide selected from a pentapeptide, hexapeptide, or mixtures thereof, at least one extract from *Laminaria* genus, and whey protein.

DETAILED DESCRIPTION

The composition of the invention may be in the liquid, semi-solid, or solid form, and may be in the emulsion, solution, suspension, or anhydrous form. If in the solution or suspension form, the composition may contain from about 50 to 99.9% water. If in the emulsion form, the composition may contain from about 5-95% water and from about 5-95% oil. If in the anhydrous form, the composition may comprise from about 10-99% oil and 10-99% solidifying agents.

I. The Tripeptide or Tetrapeptide

The composition of the invention contains at least one tripeptide or tetrapeptide, or mixtures thereof. Suggested ranges are from about 0.000001 to about 10%, preferably from about 0.000005 to 5%, more preferably from about 0.00001 to 2.5%.

A particularly preferred tripeptide has the INCI name Tripeptide-32 and has the following amino acid sequence:

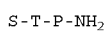

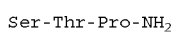

A particularly preferred tetrapeptide has the INCI name Tetrapeptide-26 which has the amino acid sequence:

(SEQ ID No. 1)

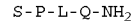

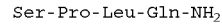

These peptides are manufactured by ISP-Vinscience under the trademark Chronolux® having the INCI name Tripeptide-32 or Chronogen® having the INCI name Tetrapeptide-26.

The Pentapeptide or Hexapeptide

The composition contains at least one pentapeptide or hexapeptide or mixtures thereof in an amount ranging from about 0.000001 to 5%, preferably from about 0.00001 to 2%, more preferably from about 0.0005 to 1% by weight of the total composition.

The pentapeptide or hexapeptide may be substituted with acyl groups such as acetyl, palmitoyl, myristoyl and the like. Further specific examples include hexapeptides 1-60, said range including each whole integer between 1 and 60, hexapeptides that are acetylated, palmitoylated or myristoylated such as acetyl hexapeptides 1, 7, 8, 19, 20, 22, 24, 30, 31, 37, 38, 39, or 40. Particularly preferred is Acetyl Hexapeptide-8 which is obtained by the acetylation of Hexapeptide-8, a synthetic peptide containing arginine, glutamic acid, glutamine, and methionine. Acetyl Hexpeptide-8, represented by sequence listing (SEQ ID No. 2)

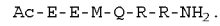

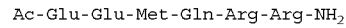

can be purchased from Lipotec S.A. under the trade name Argireline®, which is a solution of about 0.05 parts Acetyl Hexpeptide-8, 99.35 parts water, with the remainder preservatives.

Also suitable are pentapeptides which may be acetylated, palmitoylated, or myristoylated. Examples of such pentapeptides include Pentapepides 1-50 which includes each integer inbetween. Particularly preferred is Palmitoyl pentapeptide-5.

Particularly preferred are oligopeptides having the INCI names Acetyl-hexapeptide-8, Palmitoyl hexapeptide-12, Pentapeptide-3, Palmitoyl pentapeptide-5 or combinations thereof.

These peptides are defined by the International Nomenclature for Cosmetic Ingredients (INCI) and are terms known in the art.

The Extract from *Laminaria* Genus

The composition contains at least one extract from the *Laminaria* genus. *Laminaria* is a genus that contains 30+ species of the brown algae Phaeophyceae, often referred to as kelp. Such extracts from the *Laminaria* genus include those of species *abyssalis, agardhii, appressirhiza, brasiliensis, brongardiana, bulbosa, bullata, complanata, digitata, ephemera, farlowii, groenlandica, hyperborea, inclinitorhiza, multiplicata, nigripes, ochroleuca, pallida, platymeris, rodriguezi, ruprechtii, sachalinensis, setchellii, sinclairii, solidungula,* or *yezoensis*. Preferred is where the extract from the *Laminaria* genus is also an activator of Sirtuin 3. Preferred is where the extract is from *Laminaria digitata*, and more specifically an extract having laminarin content and/or a mannitol content ranging from 0.5 to 3% by weight, or from about 0.75 to 2.5%, by weight, or most preferably from about 1% by weight or greater, preferably around 2%. An example of a suitable extract of *Laminaria digitata* may be purchased from Barnet Products under the tradename Mitostime Di which is a mixture of 91 parts water, 8 parts *Laminaria digitata* extract, and 1 part preservative. Preferably the *Laminaria digitata* extract is obtained by aqueous extraction and leaching of lyophilized algae and sterilizing the microfiltration, followed by reverse osmosis to concentrate the active molecules.

In the preferred embodiment of the invention the *Laminaria* extract may be present in the composition in amounts ranging from 0.0001 to 5%, preferably from about 0.001 to 2.5%, more preferably from about 0.01 to 1%.

Whey Protein

The composition contains whey protein, in an amount ranging from 0.01 to 5%, preferably from about 0.05 to 3%, more preferably from about 0.1 to 2% by weight of the total composition.

Whey protein is the polypeptide obtained from the fluid part of milk after separation from curds. The whey protein may be hydrolyzed. Most preferred is a whey protein sold by Glanbia Foods having the trade name whey protein NXP.

In one embodiment, the pentapeptide or hexapeptide, *Laminaria* extract and whey protein may be supplied to the composition in the form of a pre-blend that can then be formulated into the final product. In this case a ratio of from about 2-20 parts of pentapeptide or hexapeptide, 1-10 parts *Laminaria* extract, and 0.1 to 5 parts whey protein is appropriate. Most preferred is a ratio of 10 parts Acetyl hexapeptide-8, 5 parts *Laminaria digitata* extract, and 1 part whey protein.

The composition of the invention, which is a collagen synthesis stimulating composition, may consist of the first peptide which is the tri- or tetrapeptide or mixtures thereof, the second peptide which is the penta- or hexapeptide or mixtures thereof, the extract from the *Laminaria* genus, and whey protein and no other ingredients.

The composition of the invention may also "consist essentially of" the first peptide which is the tri- or tetrapeptide; the second peptide which is the penta- or hexapeptide, the extract from the *Laminaria* genus, and whey protein, which means a composition that contains the four ingredients and only additional ingredients that do not affect that basic and novel characteristics of the composition such as water, preservatives, antioxidants, pH adjusters, solvents, and inert ingredients such a silicones that do not affect the collagen stimulating activity of the composition.

The composition of the invention may also "comprise" the four ingredients mentioned and include other ingredients including but not limited to those set forth herein.

Other Ingredients

Oils

Suitable oils include silicones, esters, vegetable oils, synthetic oils, including but not limited to those set forth herein. The oils may be volatile or nonvolatile, and are preferably in the form of a pourable liquid at room temperature. If present, the oils may range from about 0.5 to 85%, preferably from about 1-75%, more preferably from about 5-65% by weight of the total composition.

Cyclic and linear volatile silicones are available from various commercial sources including Dow Corning Corporation and General Electric. The Dow Corning linear volatile silicones are sold under the trade names Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

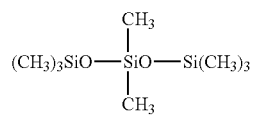

Methyl trimethicone may be p purchased from Shin-Etsu Silicones under the trade name TMF-1.5, having a viscosity of 1.5 centistokes at 25° C.

Also suitable are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

Also suitable are esters formed by the reaction of a carboxylic acid and an alcohol. The alcohol and the carboxylic acids may both have fatty (C6-30) chains. Examples include hexyl laurate, butyl isostearate, hexadecyl isostearate, cetyl palmitate, isostearyl neopentanoate, stearyl heptanoate, isostearyl isononanoate, stearyl lactate, stearyl octanoate, stearyl stearate, isononyl isononanoate, and so on.

The ester may also be in the dimer or trimer form. Examples of such esters include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Examples of other types of esters include those from arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisostearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone. Examples include dimethicone, phenyl dimethicone, diphenyl dimethicone, phenyl trimethicone, or trimethylsiloxyphenyl dimethicone. Other examples include alkyl dimethicones such as cetyl dimethicone, stearyl dimethcone, behenyl dimethicone, and the like.

Surfactants

The composition may contain one or more surfactants, especially if in the emulsion form. However, such surfactants may be used if the compositions are anhydrous also, and will assist in dispersing ingredients that have polarity, for example pigments. Such surfactants may be silicone or organic based. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

Silicone surfactants may be generically referred to as dimethicone copolyol or alkyl dimethicone copolyol. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Coming 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of crosslinked silicone surfactants that are often referred to as emulsifying elastomers that contain at least one hydrophilic moiety such as polyoxyalkylenated groups. Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on. All recitations of units include all whole integers between the range.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

Humectants

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

Botanical Extracts

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina Pavonica* extract, *thermus thermophilis* ferment extract, camelina sativa seed oil, boswellia serrata extract, olive extract, *Aribodopsis Thaliana* extract, *Acacia Dealbata* extract, *Acer Saccharinum* (sugar maple), acidopholus, acorus, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza Glabra, Salix Nigra, Macrocycstis Pyrifera, Pyrus Malus, Saxifraga Sarmentosa, Vitis Vinifera, Morus Nigra, Scutellaria Baicalensis, Anthemis Nobilis, Salvia Sclarea, Rosmarinus Officianalis, Citrus Medica Limonum, Panax Ginseng, Siegesbeckia Orientalis, Fructus Mume, Ascophyllum Nodosum*, Bifida Ferment lysate, *Glycine Soja* extract, *Beta Vulgaris, Haberlea Rhodopensis, Polygonum Cuspidatum, Citrus Aurantium Dulcis, Vitis Vinifera, Selaginella Tamariscina, Humulus Lupulus, Citrus Reticulata Peel, Punica Granatum, Asparagopsis, Curcuma Longa, Menyanthes Trifoliata, Helianthus Annuus*, Hordeum Vulgare, *Cucumis Sativus, Evernia Prunastri, Evernia Furfuracea*, and mixtures thereof.

Particulate Materials

The compositions of the invention may contain particulate materials in the form of pigments, inert particulates, or mixtures thereof. If present, suggested ranges are from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

The particulate matter may be colored or non-colored powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

Suitable pigments are organic or inorganic. Organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

Vitamins and Antioxidants

The compositions of the invention may contain vitamins and/or coenzymes, as well as antioxidants. If so, 0.001-10%, preferably 0.01-8%, more preferably 0.05-5% by weight of the total composition is suggested. Suitable vitamins include ascorbic acid and derivatives thereof such as ascorbyl palmitate, tetrahexydecyl ascorbate, and so on; the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are retinyl palmitate, retinol. retinoic acid, as well as Vitamin A in the form of beta carotene. Also suitable is Vitamin E and derivatives thereof such as Vitamin E acetate, nicotinate, or other esters thereof. In addition, Vitamins D and K are suitable.

The invention further comprises treating skin to stimulate collagen synthesis by topically applying a composition tri- or tetrapeptide, at least one penta- or hexapeptide, at least one extract from the *Laminaria* genus, and whey protein. The compositions may be applied in the forms mentioned herein, as part of skin care regimens. For example, the composition may be applied to the skin as a night cream or cream applied to skin prior to a period of bodily rest such as a nap or sleep. The composition may be applied two times a day, in the morning and in the evening after cleansing the skin. The composition may be applied to the skin over skin care products, in the form of foundations or other color cosmetics.

The invention will be further described in connection with the following examples which are set forth for the purposes of illustration only.

Example 1

Tripeptide-32 was tested at various concentrations for its ability to stimulate collagen production in normal human dermal fibroblasts ("NHDF") from a 62 year old donor in a collagen induction assay. Tripeptide-32 was tested at 1× (0.2%) 0.5× (0.1%) and 0.2× (0.04%) concentration diluted in DMEM ("Dulbecco's Modified Eagle Medium") supplemented with 10% Hyclone® bovine calf serum and 1% Cellgro® penicillin-streptomycin solution ("DMEM"). All percentages are by weight of the total composition.

Cell Growth and Maintenance.

Aged NHDF were obtained from ZenBio. Fibroblasts were cultured in DMEM 1× (Life Tech) supplemented with 10% bovine calf serum ("BCS") (Hyclone) and 1% PenStrep ("PS") solution (Cellgro). Cells were regularly maintained; subcultured as needed.

Plating Cells.

Normal human dermal fibroblasts (NHDF, aged) were plated on a 96-well plate in supplemented DMEM (as indicated above). All rows, except for Row A, were seeded with cells (Row A was left blank to allow for background subtraction). Plate was allowed to incubate at standard conditions (37° C., 5% $CO_2$, 95% humidity) overnight.

Preparation & Treatment of Cells.

The following treatments were created in full media (1% P/S and 10% BCS supplemented) DMEM: (1) *Laminaria digitata* extract (0.5%); Acetyl hexapeptide-8 solution (a mixture of 0.05% Acetyl hexapeptide-8, 99.35% water and the remainder preservatives) (10%); and whey protein (0.1%, solid) with the remainder DMEM (the "Mixture"); (2) Mixture+Tripeptide-32: *Laminaria digitata* extract (0.5%), Acetyl hexpeptide-8 solution (10%), whey protein (0.1%) and Tripeptide-32 (0.2%) in DMEM at 1× (0.2%), 0.5× (0.1%), and 0.2× (0.04%) concentration; (3) Tripeptide-32 alone at 1× (0.2%), 0.5× (0.1%) and 0.2× (0.04%) concentration. Each treatment (200 ul/well) was added to the corresponding well of the 96-well plate. Treated plate was allowed to incubate at standard conditions (37° C., 5% $CO_2$, 95% humidity) for 5 days.

Viability Assay.

Following 5 days of incubation, supernatants were harvested and stored prior to collagen analysis. A 10% alamar blue (Life Tech) solution was created in warmed (37° C.) full media and assay was completed exactly as per manufacturer's (Life Tech) protocol. Alamar Blue results were determined using a plate reader. Data was analyzed using the SoftMax Pro software and Excel.

Assessment of Collagen Production.

Collagen production was assessed using the Pro-collagen Type I collagen EIA Kit (Takara) as per manufacturer's protocol, exactly as described. Plate was read using the Gemini M2E plate reader and results were compared.

The results are set forth below and show that Tripeptide-32 alone shows decreased collagen synthesis at 0.2× (0.04%), and nearly insignificant increase in collagen synthesis at 0.5× (0.1%) and 1× (0.2%) concentrations. The Mixture of Acetyl hexapeptide-8, *Laminaria digitata* extract, and whey protein demonstrates increased collagen synthesis. However, there is a synergistic increase in collagen synthesis when Tripeptide-32 is combined with the Mixture.

| Test Material | Concentration | % increase in collagen induction |
| --- | --- | --- |
| DMEM | Neat (Control) | 0 |
| Tripeptide-32 | 0.2X | −15.39 |
| Tripeptide-32 | 0.5X | +1.17 |
| Tripeptide-32 | 1.0X | +3.27 |
| Mixture alone | 0.2X | +129.50 |
| Mixture alone | 0.5X | +165.08 |
| Mixture alone | 1.0X | +200 |
| Mixture + Tripeptide-32 | 0.2X | +148.13 |
| Mixture + Tripeptide-32 | 0.5X | +214.57 |
| Mixture + Tripeptide-32 | 1.0X | +267.14 |

In general it is seen that when Tripeptide-32 is combined with the mixture of Acetyl hexapeptide-8, *Laminaria digitata* extract, and whey protein there is a synergistic increase in collagen synthesis in cells which is unexpected given that Tripeptide-32 alone causes decreased collagen synthesis, or at best very marginal insignificant increases in collagen synthesis. Thus, this combination stimulates collagen synthesis in skin cells.

Example 2

The combination of Tripeptide-32 and a mixture of Acetyl hexapeptide-8, *Laminaria digitata* extract and whey protein were tested for collagen stimulation in NHDF from a 62 year old donor. Tripeptide-32 at a concentration of 0.2% was combined with a mixture of Acetyl hexapeptide-8 solution (0.05% Acetyl hexapeptide-8, 99.35% water, remainder preservatives) (10%); 0.5% *Laminaria digitata* extract solution, and 0.1% whey protein in Supplemented DMEM.

The tests were performed according to the method in Example 1. The results are set forth below:

| Test Material: | Percent Increase in Collagen Synthesis over Mixture Alone (%) |
| --- | --- |
| 0.2X Mixture + 0.2X Tripeptide-32 | +8.44 |
| 0.5X Mixture + 0.5X Tripeptide-32 | +18.67 |
| 1.0X Mixture + 1.0X Tripeptide-32 | +22.38 |

The above results show that addition of increasing concentrations of Tripeptide-32 extract to increasing concentrations of the Mixture provided a dose response increase in collagen synthesis in fibroblasts. As noted in Example 1, Tripeptide-32 itself largely causes decreased collagen synthesis in fibroblasts, and exhibits no dose response relationship to increasing concentrations.

Example 3

A skin care composition according to the invention was made as follows:

| Ingredient | % by weight |
| --- | --- |
| Water | QS100 |
| Isononyl isononanoate | 6.0 |
| C12-20 acid PEG-8 ester | 3.0 |
| Glycerin | 2.6 |
| Dimethicone | 1.5 |
| Shea butter | 1.5 |
| Cetyl alcohol | 1.4 |
| Butylene glycol | 1.2 |
| PEG-100 stearate | 0.75 |
| Acetyl glucosamine | 0.50 |
| Sucrose | 0.50 |
| Preservatives | 1.0 |
| Ammonium acryloyldimethyl taurate | 0.35 |
| Sorbitol | 0.35 |
| Pentylene glycol | 0.25 |
| Algae extract | 0.25 |
| Caffeine | 0.20 |
| Carbomer | 0.20 |
| Potassium cetyl phosphate | 0.20 |
| Tocopheryl acetate | 0.20 |
| Ethylhexylglycerin | 0.15 |
| Aquacell* | 1.00 |
| Acrylates/C10-30 alkyl acrylates crosspolymer | 0.11 |
| Phytofix** | 0.20 |
| Whey protein | 0.10 |
| Glucose | 0.10 |
| Isoceteth-20 | 0.10 |
| *Laminaria digitata* extract | 0.04 |

-continued

| Ingredient | % by weight |
|---|---|
| Acetyl hexapeptide 8 | 0.01 |
| Tripeptide-32 | 0.20 |

*Aquacell: a mixture of water, Citrullus lanatus (watermelon) fruit extract, Pyrus malus (apple) fruit extract, Lens esculenta (Lentil) fruit extract, sodium lactate, and sodium PCA.
**Phytofix: a mixture of propylene glycol dicaprate, Helianthus annus (sunflower) seed cake, Hordeum vulgare (barley) extract, Cucumis sativus (cucumber) fruit extract.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

The invention claimed is:

1. A composition comprising a first peptide selected from the group consisting of Tripeptide-32, Tetrapeptide-26, and mixtures thereof; a second peptide selected from the group consisting of a pentapeptide selected from the group consisting of Pentapeptide-3, Palmitoyl pentapeptide-5 and mixtures thereof, a hexapeptide selected from the group consisting of Palmitoyl hexapeptide-12, Acetyl hexapeptide-8, and mixtures thereof; at least one extract from the Laminaria genus; and whey protein.

2. The composition of claim 1 wherein the first peptide is Tetrapeptide-26.

3. The composition of claim 1 wherein the first peptide is Tripeptide-32 and is present at 0.000001 to about 10%.

4. The composition of claim 1 wherein the second peptide is a hexapeptide.

5. The composition of claim 4 wherein the hexapeptide is Palmitoyl hexapeptide-12.

6. The composition of claim 4 wherein the acetylated hexapeptide is Acetyl hexapeptide-8 and is present at 0.000001 to 5%.

7. The composition of claim 1 wherein the first peptide is a tripeptide that is Tripeptide-32, the second peptide is a hexapeptide that is Acetyl hexpetide-8, and the extract from the Laminaria genus is from Laminaria digitata.

8. The composition of claim 7 wherein the extract from Laminaria digitata has a laminarin or mannitol content of 0.5 to 3% by weight of the total extract.

9. The composition of claim 8 wherein the Laminaria digitata extract is obtained by aqueous extraction and leaching of lyophilized algae.

10. The composition of claim 8 wherein the Laminaria digitata extract is present from 0.0001 to 5%.

11. A composition comprising, by weight of the total composition:

0.000001 to 10% Tripeptide-32, 0.000001 to 5% Acetyl hexapeptide-8, 0.0001 to 5% Laminaria digitata extract, 0.05 to 3% whey protein.

12. The composition of claim 11 wherein the *Laminaria digitata* extract has a laminarin or mannitol content ranging from 0.5 to 3% by weight of the total extract.

13. The composition of claim 12 wherein the *Laminaria digitata* extract is obtained by aqueous extraction and leaching of lyophilized algae.

14. The composition of claim 11 in the form of a skin cream, lotion, foundation makeup, or gel.

15. A method for stimulating collagen synthesis in skin cells by topically applying the composition of claim 1.

16. The method of claim 15 wherein the composition is in the form of a skin cream or lotion.

17. The method of claim 16 wherein the composition is applied once or twice per day.

18. The method of claim 16 wherein the first peptide is a tripeptide that is Tripeptide-32, the second peptide is a peptide that is Tetrapeptide-26, and the extract from the *Laminaria* genus is from *Laminaria digitata*.

19. The method of claim 18 wherein the Tripeptide-32 is present at 0.000001 to 10%, the Acetyl hexapeptide-8 is present at 0.000001 to 5%, the *Laminaria digitata* extract is present at 0.0001 to 5%, and the whey protein is present at 0.05 to 3%.

20. The method of claim 19 wherein the composition is applied at night prior to retiring.

21. A collagen stimulating composition comprising Tripeptide-32 in combination with a mixture of *Laminaria digitata* extract, whey protein, and Acetyl hexapeptide-8.

22. The collagen stimulating composition of claim 21 showing a greater than additive increase in collagen synthesis when compared to the collagen stimulating activity of Tripeptide-32 alone and the mixture of *Laminaria digitata* extract, whey protein, and Acetyl hexapeptide-8 alone.

23. The collagen stimulating composition of claim 21 wherein the collagen stimulating activity is characterized by showing a synergistic increase in collagen synthesis when tested on fibroblasts in vitro.

* * * * *

UNITED STATES PATENT AND TRADEMARK OFFICE
CERTIFICATE OF CORRECTION

PATENT NO. : 10,149,811 B2  
APPLICATION NO. : 15/041602  
DATED : December 11, 2018  
INVENTOR(S) : Nadine Pernodet and Krystle Corallo Page 1 of 1

It is certified that error appears in the above-identified patent and that said Letters Patent is hereby corrected as shown below:

In the Claims

In Column 13, Line 17, Claim 18 please delete the term "Tetrapeptide-26" and include the term "Acetyl hexapeptide-8".

Signed and Sealed this
Twenty-first Day of January, 2020

Andrei Iancu
*Director of the United States Patent and Trademark Office*

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)
<223> OTHER INFORMATION: The C-terminus carboxyl group of Gln is
      replaced with NH2

<400> SEQUENCE: 1

Ser Pro Leu Gln
1

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)
<223> OTHER INFORMATION: The N-terminus Glu is acetylated
<220> FEATURE:
<221> NAME/KEY: misc_feature
<222> LOCATION: (6)
<223> OTHER INFORMATION: The C-terminus carboxyl group of Arg is
      replaced with NH2

<400> SEQUENCE: 2

Glu Glu Met Gln Arg Arg
1               5
```